United States Patent [19]

Oka et al.

[11] Patent Number: 5,498,541
[45] Date of Patent: Mar. 12, 1996

[54] METHOD FOR PRODUCING POTATO MICROTUBERS

[75] Inventors: Ichiro Oka, Iwata, Japan; Carolyn Sluis, Davis, Calif.

[73] Assignee: Japan Tobacco Inc., Tokyo, Japan

[21] Appl. No.: 159,491

[22] Filed: Nov. 30, 1993

[51] Int. Cl.$^6$ .............................. C12N 5/04; A01C 1/00
[52] U.S. Cl. .................. 435/240.45; 435/240.51; 435/240.54; 47/58; 47/DIG. 3; 47/DIG. 6
[58] Field of Search ............................ 435/240.4, 240.45, 435/240.46, 240.51, 240.54; 47/58, DIG. 3, DIG. 6; 800/DIG. 40

[56] References Cited

U.S. PATENT DOCUMENTS 5,034,327  7/1991  Takayama et al. .................. 435/240.4

FOREIGN PATENT DOCUMENTS 0476141    3/1992   European Pat. Off. .
3734257    4/1989   Germany .
3-35738    2/1991   Japan .
WO89/10399 11/1989  WIPO .

OTHER PUBLICATIONS

T. Murashige et al. (1962) *Physiologia Plantarum* 15:473–497.

G. Hussey et al. (1981) *Ann. Bot.* 48:787–796.

E. Linsmaier et al. (1965) *Physiologia Plantarum* 18:100–127.

P. Wang et al. (1982) *American Potato Journal* 59:33–37.

R. Estrada et al. (1986) *Plant Cell, Tissue & Organ Culture* 7:3–10.

P. White (1963) *The Cultivation of Animal and Plant Cells*, The Ronald Press Co., NY, pp. 57–63.

P. Li (1985) *Potato Physiology*, Academic Press, Inc., Orlando, pp. 544–551.

Abbott et al. 1986. In Plant Tissue Culture and its Agricultural Applications. Ch 11:113–122. Withers et al., eds.

Hussey et al. 1984. Annals of Botany. 53:565–578.

*Primary Examiner*—David T. Fox
*Assistant Examiner*—Erich E. Veitenheimer
*Attorney, Agent, or Firm*—Birch, Stewart, Kolasch & Birch

[57] ABSTRACT

An improved method for producing potato microtubers by tissue culture is provided. The improvement comprises culturing potato plants in a medium containing a high sugar content, i.e., 8% (w/v), for about 1 to 4 weeks under the light prior to culturing the plants in the dark to produce the microtubers.

20 Claims, No Drawings

METHOD FOR PRODUCING POTATO MICROTUBERS

BACKGROUND OF THE INVENTION

1. Field of the Invention

The present invention relates to a method for producing potato microtubers whereby large microtubers which can be directly planted in the field are efficiently produced.

2. Description of Related Art

A first method for producing potato microtubers that is popularly employed in practice comprises the steps of growing virus-free plants and then forming and growing microtubers.

A second method is described in Japanese Laid-open Patent Application No. 3-35738. This Laid-open Patent Application discloses a process for producing potato microtubers comprising the following three steps:

(A) Potato plants are tissue-cultured to produce virus-free plants having stems and leaves (Illumination: 1,000–100,000 lux for 6–24 hours/day, at 20°–30° C.);

(B) The plants are cultured at a low temperature (10°–30° C.) under a short daylength (1,000–100,000 lux for 12 hours or less), thereby inducing a state in which the apical buds or axillary buds are converted to microtubers;

(C) Apical buds or axillary buds induced in the preceding step are converted into microtubers in the dark at a low temperature (10°–30° C.).

In the second method, a step of inducing the state in which the apical buds and axillary buds are converted to microtubers at low temperature and under a short daylength is inserted between the two steps of the first method. This step was presumably inserted taking into consideration the general property of potatoes that the formation of microtubers is induced at a low temperature and under a short daylength, which property is known and described in the literature.

Thus, via the second method, microtubers are effectively produced by three steps, i.e., step A: growth of virus-free plants; step B: induction of the state in which the apical buds and axillary buds are converted into microtubers; and step C: formation and growth of microtubers.

It is another characteristic feature of the second method that step C is carried out at a low temperature in the dark. In general, the formation and growth of the microtubers are carried out in the dark or under a short daylength. Although the reason why the low temperature condition is indispensable is not clear, it is probably because the formation of potato microtubers is promoted at low temperature.

It seems true that the conversion into microtubers is promoted, and the number of formed microtubers is increased, by the short day treatment after the stem and leaf-growing step. However, since the efficiency of production of large microtubers (not less than 0.5 g) which can be directly planted in the field is low due to the following reasons, this method is not practical.

In the second method, subsequent to the plant-growing step, microtubers are induced at a low temperature and under a short daylength using the same medium as used in the plant-growing step. This medium has a low sugar content, and immediately after exchanging the medium with one having a high sugar content, the potato plants are cultured in the dark to form microtubers. Since the potato plants are cultured on a medium having a low sugar content at a low temperature under a short daylength at the stage in which the growth of stems and leaves is active, the growth of plants is not good, and even if the number of total microtubers is increased, the number of large microtubers is very small.

Since the growth of plants and the induction of the converting state into microtubers are carried out using an agar medium in a small vessel (0.3–0.6 liter), the efficiency of growth of plants is lower than in the case where culturing is carried out by liquid aeration culture using a large vessel. Thus, the practical production of large microtubers cannot be attained by this method.

In Japanese Laid-open patent application (Kokai) No. 3-35738 (second method), the conditions of steps B and C are "at a low temperature and under short daylength" and "in the dark and at low temperature," respectively. Thus, in both steps, low temperature is indispensable. However, the temperature conditions employed in two examples are ordinary temperature conditions which are generally employed in the tissue culture of potatoes. The temperature conditions are also within the known range employed in the production of microtubers.

SUMMARY OF THE INVENTION

An object of the present invention is to provide a method for producing potato microtubers by which large microtubers which can be directly planted in the field are efficiently produced. This is achieved by culturing potato plants on a medium containing a high sugar content for about 1 to about 4 weeks under the light prior to culturing said plants in the dark to produce said microtubers.

Further scope of the applicability of the present invention will become apparent from the detailed description provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The following detailed description is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

As employed below, the phrase "daylength" includes either a short daylength or a long daylength.

"Short daylength" preferably denotes illumination for about 6 to about 12 hours, more preferably about 7 to about 10 hours, and most preferably about 8 hours during a 24 hour growth cycle.

"Long daylength" preferably denotes illumination for about 12 to about 24 hours, more preferably about 14 to about 20 hours, and most preferably about 16 hours during a 24 hour growth cycle.

Step (1): Growing Plants

Virus-free plantlets of potato which are grown essentially by the method of Hussey et al. (1981) *Ann. Bot.* 48:787–796 are cut into nodal cuttings, each of which contains a single node (or into sections containing two or more nodes), each of which has axillary buds and leaves. The axillary buds grow into plants. The resulting nodal cuttings are placed in the vessels listed in Table 1, and plants are grown by liquid aeration culture at 18°–25° C., preferably 18°–22° C., under an illumination of 3,000–10,000 lux, preferably 4,000–6,000 lux, for 12–24 hours a day (i.e., a long daylength). The medium can be Murashige & Skoog's medium (Murashige et al. (1962) *Physiol. Plant.* 15:473–497, hereinafter referred to as "MS medium"), containing 2% (w/v) of sucrose, pH 5.8. This medium is hereinafter referred to as "plant-growing medium." "Whit's Medium" (White (1963) *The Cultivation of Animal and Plant Cells*), "Linsmayer and Skoog's Medium" (Linsmayer and Skoog (1965) *Physiol. Plant.* 18), and other standard plant tissue culture media can also be employed in place of "MS medium." As the sugar (carbon source) in the medium, glucose, fructose, maltose, etc. can be employed in place of sucrose. The sugar concentration can be in the range from 0.5–5%, preferably 2–3%, and the pH can be in the range from 4–8, preferably 5.5–6.5.

The number of nodal cuttings (explants) cultured, the amount of medium, and the rate of aeration per vessel differ depending on the size of the vessel listed in Table 1. The number of explants can be 1–30, preferably 10–20, per liter of medium. The volume of medium per 1 liter vessel can be 0.1–0.5 liters, preferably 0.2–0.3 liters. The rate of aeration can be 0.02–0.5 liter/liter.min., preferably 0.2–0.4 liter/liter.min.

TABLE 1

| Volume of Vessel | Number of Nodal Cuttings Placed in One Vessel | Amount of Medium (L) | Rate of Aeration (L/min) | Size of Vessel | | Seller |
|---|---|---|---|---|---|---|
| | | | | Diameter | Height | |
| 2L | 8 | 0.6–0.7 | 0.35–0.4 | 13 cm | 18 cm | * |
| 4L | 14–16 | 1.0 | 0.7–0.8 | 15 cm | 22 cm | * |

*Carolina Biological Supply Company

Air was blown into the liquid medium at the bottom of the vessel.

In 3–6 weeks from the beginning of culture, the plants have usually grown to a height about 80% of the height of the vessel.

Step. (2): Induction of the State in Which Buds are Converted Into Microtubers

In the above-mentioned step, when the heights of the plants reach about 80% of the height of the vessel (no problems are encountered if the height is at least about 50% of the height of the container), the remaining medium is discarded and a medium containing 6–10% (w/v) sugar, preferably 7–9% (w/v) sugar, especially 8% (w/v) sugar, hereinafter referred to as "microtuber-forming medium," is placed in the vessel in the amount shown in Table 1. Sugars useful in the present step include sucrose, glucose, fructose, and maltose. The medium can be any of the media noted above in step (1). Thereafter, the plants are cultured for 1–4 weeks under long daylength or short daylength. If it is desired to obtain a number of small microtubers, the plants are cultured under a short daylength for about one week; if it is desired to obtain large microtubers, the plants are cultured under a long daylength for about two weeks. The illumination intensity, temperature, medium volume, and the rate of aeration are the same as those in the plant-growing step (1) described above.

Step (3): Forming and Growing Microtubers

After the above-described step (2), the plants are cultured for 3–10 weeks, preferably for 5–9 weeks, under the same conditions as in step (2), except that the plants are cultured in the dark, and the microtubers are harvested.

In the method employing the short daylength, formation of microtubers is observed before or after several days from the beginning of the culture in the dark. In the method employing the long daylength, formation of microtubers is observed after 1–2 weeks from the beginning of the culture in the dark. Within 4–5 weeks from the beginning of the culture in the dark, each of the microtubers is considerably grown and the growth thereafter is slowed. Although the microtubers can be harvested after about 5 weeks from the beginning of the culture in the dark, to obtain mature microtubers, it is preferable to harvest the microtubers after at least a part of the stems and leaves have started to senesce.

Differences Between the Present Invention and Prior Art Methods

A characteristic feature of the method of the present invention is that the plants are made to effectively absorb a medium having a high sugar content under illumination so as to sufficiently absorb and store nutrients in the stems and leaves so that microtubers are effectively produced in the subsequent dark step.

In the second conventional method described supra, only the fact that the formation of microtubers is promoted "at low temperature condition and under short daylength" is taken into consideration. Consequently, after the step of growing plants, the conversion into microtubers is induced "at a low temperature and under a short daylength," and then the medium is replaced with one having a high sucrose content, followed by culturing the plants in the dark to form and grow microtubers. Thus, the second conventional method only considers inducing the formation of microtubers under a short daylength. The idea of promoting the growth of the plants is not considered.

In the first and second conventional methods, immediately after replacing the medium with one having a high sugar content for the formation of microtubers, the plants are cultured in the dark to form microtubers. However, the absorption of the medium by the plants is slow in the dark, so that the medium enriched in nutrients is not effectively absorbed by the plants.

The method of the present invention overcomes these drawbacks. Although the method of the present invention is the same as the second conventional method in that it contains three steps, the second step is not merely for inducing the formation of microtubers under the short daylength. In the second step of the method of the present invention, the plants are cultured under the light for 1–4 weeks after changing the medium with one having a high sugar content so as to make the plants efficiently absorb the medium containing a high level of nutrients. After sufficiently storing nutrients in the stems and leaves in the second step, the plants are cultured in the dark to form microtubers. Since large amounts of nutrients are stored in the stems and leaves, microtubers are efficiently formed.

That is, before culturing the plants in the dark, under which condition the absorption of nutrients is slow, the energy for forming and growing microtubers is stored in the stems and leaves under the light as much as possible, and microtubers are then formed and grown efficiently in the dark using the stored energy.

Effects of the Present Invention

Increase in the Total Number of Microtubers Per Vessel and Increase in the Number of Large Microtubers The efficiency of production of microtubers by the method of the present invention is higher than those in the first and second conventional methods (see Table 2) in which microtubers are formed in the dark after replacing the medium with one having a high sucrose content after the short daylength treatment.

Although the total number of microtubers including small microtubers with weights of not more than 0.1 g was larger in the second conventional method than that obtained by the first conventional method, the number of microtubers with weights of not less than 0.1 g in the second conventional method was about the same as that obtained by the first conventional method, and the number of microtubers with weights of not less than 0.5 g obtained in the second conventional method was considerably smaller than that obtained by the first conventional method. Thus, the second conventional method is not efficient since what is desired are microtubers having a weight of not less than 0.5 g. If the microtuber has a weight of not less than 0.5 g, it can be directly planted and grown in the field. If the microtuber has a weight of less than 0.5 g, the growth of a plant thereof is slow if it is directly planted in the field.

According to an embodiment of the present invention wherein 8 hours daylength is employed after replacing the medium, the efficiency of production of microtubers having weights of not less than 0.1 g was much higher than those attained in the first and second conventional methods, and the total number of microtubers was also increased. Further, the number of microtubers having weights of not less than 0.5 g was also larger.

According to an embodiment of the present invention wherein 16 hours daylength is employed after replacing the medium, the number of large microtubers having weights of not less than 0.5 g or not less than 1 g was much larger than those attained by the first and second conventional methods. Furthermore, the number of microtubers having weights of not less than 0.1 g was also larger.

Production of Mature Microtubers

By culturing the plants under illumination (5,000 lux) after replacing the medium, not only are the stems and leaves well developed and the number of microtubers produced increased, but the medium is also rapidly absorbed by the plants. Therefore, the time at which the leaves and stems turned yellow and started to senesce in the later stage of the microtuber growing step was early, so that mature, high quality microtubers which are suited for storing and cultivation in the field were obtained.

EXAMPLE 1

Influence of the Daylength Regimen on Microtuber Production Before and After Replacement of the Medium Virus-free plants grown essentially by the method of Hussey et al. (1981) Ann. Bot. 48:787–796 (variety: Russet Burbank, plants stored in Tissue-Grown Corporation were grown) were cut into nodal cuttings, each of which contained a single node, and eight nodal cuttings were placed per glass vessel having an inner volume of 2 liters, a diameter of 13 cm, and a height of 18 cm, which contained 0.6 liters of the plant-growing medium. Such glass vessels are commercially available from Carolina Biological Supply Company, and are hereinafter referred to as "2L-vessels" The plants were cultured at 20° C. under an illumination of 5,000 lux for 16 hours/day and at an aeration rate of 0.35–0.4 liters/min.

The plants grew to an average length of 15 cm after about 4 weeks from the beginning of the cultivation.

Then, one of the following steps a) to d) was carried out:

a) After culturing the plants for 4 weeks under the conditions described above, the remaining medium was removed and replaced with 0.7 liters of the microtuber-forming medium, and culturing was continued for another 18 days at 20° C. under an illumination of 5,000 lux for 8 hours a day at an aeration rate of 0.35–0.4 liters/min. (the present invention).

b) After culturing the plants for 4 weeks under the conditions described above, the medium was replaced as in above-mentioned step a), and culturing was continued for another 25 days at 20° C. under an illumination of 5,000 lux for 16 hours a day at an aeration rate of 0.35–0.4 liters/min. (the present invention).

c) After culturing the plants for 4 weeks under the conditions described above, culturing was continued for another 17 days under the same conditions, except that the day length was changed to 8 hours. Thereafter, the remaining medium was removed and 0.7 liters of the microtuber-forming medium was added (second conventional method).

TABLE 2

Effects of Illumination Before and After Replacement of Medium; Variety: Russet Burbank

| Method | Number of Microtubers (Microtubers/vessel) | | | Weight (g/vessel) | Number of Vessels |
| --- | --- | --- | --- | --- | --- |
| | 0.1 g or more | 0.5 g or more | 1 g or more | | |
| 8 hours/day illumination after replacement of medium | 84.4** | 29.3 | 12.5 | 46.3 | 10 |
| 16 hours/day illumination after replacement of medium | 43.0 | 29.5* | 19.5 | 50.8 | 2 |
| Second Conventional Method | 40.9 | 10.9 | 4.0 | 17.1 | 7 |
| First Conventional Method (control) | 41.6 | 17.8 | 8.8 | 28.8 | 8 |

*Those having not less than 5% significance based on the control group.
**Those having not less than 1% significance based on the control group.

d) The culturing under the above-described conditions was continued for 7 weeks and then the medium was replaced (first conventional method, control).

After one of steps a) to d), the plants were cultured in the dark at 20° C. at an aeration rate of 0.35–0.4 liters/min. to form microtubers. The microtubers were harvested during the 9th week from the beginning of the culture in the dark.

The results are shown in Table 2, supra. When compared with the first conventional method (control), by the method employing step a) (i.e., 8 hours/day illumination after replacement of the medium), the number of microtubers having weights of not less than 0.1 g and of not less than 0.5 g was much greater.

By the method employing step b) (i.e., 16 hours/day illumination after replacement of the medium), although the number of microtubers having weights of not less than 0.1 g was not so different from that obtained by the first conventional method (control), the number of large microtubers having weights of not less than 0.5 g and not less than 1 g was much larger. Thus, culturing under illumination after replacement of the medium is highly effective for producing microtubers.

On the other hand, by the second conventional method employing step c) (i.e., 8 hours/day illumination before replacement of the medium), although a number of small microtubers with weights of less than 0.1 g were produced (data not shown), the number of microtubers having weights of not less than 0.1 g was about the same as in the first conventional method, and the number of microtubers with weights of not less than 0.5 g was considerably smaller than that obtained in the first conventional method. Thus, the second conventional method has no superior effects compared to the first conventional method (control).

EXAMPLE 2

The nodal cuttings from virus-free plantlets of potato (variety: Russet Burbank) were placed in the vessels and plants were grown for 4 weeks in the same manner as in Example 1, and the medium was then replaced with the microtuber-forming medium. Thereafter, one of the following steps a) to d) was carried out:

a) The plants were cultured under 8-hours daylength for 1 week and then cultured in the dark to form microtubers (the present invention).

b) The plants were cultured under 8-hours daylength for 2 weeks and then cultured in the dark to form microtubers (the present invention).

c) The plants were cultured under 16-hours daylength for 2 weeks and then cultured in the dark to form microtubers (the present invention).

d) Immediately after the replacement of the medium, the plants were cultured in the dark (first conventional method, control).

During the 9th week from the replacement of the medium, microtubers were harvested.

In this example, in addition to the above-mentioned 2L-vessels, glass vessels having an inner volume of about 4 liters with a diameter of 15 cm and a height of 22 cm (commercially available from Carolina Biological Supply Company, hereinafter referred to as "4L-vessels") were used for some groups. The culturing conditions in the 4L-vessels were the same as in the 2L-vessels, except that the number of sections placed therein was 16, the aeration rate was 0.7–0.8 liters/min., and the amount of medium (both the stem and leaf-growing medium and microtuber-forming medium) was 1 liter/vessel.

The results are shown in Table 3. As in Example 1, the number of microtubers with weights of not less than 0.1 g is increased by the 8-hour daylength treatment, and the number of microtubers with weights of not less than 0.5 g and not less than 1 g are increased in the 16-hour daylength treatment.

In the method of the present invention, the following was observed during the culture or after harvest:

(i) The plants before the culture in the dark had more stems and leaves, each leaf was thicker although somewhat smaller, and the mass of stems and leaves were more developed than those in the second conventional method.

(ii) In the method of the present invention employing 8-hour daylength, microtubers were formed after the beginning of the culture in the dark more rapidly than in the second conventional method, and formation of microtubers was observed within several days from the beginning of the culture in the dark.

TABLE 3

Effects of Illumination Before and After Replacement of Medium; Variety: Russet Burbank

| Volume of Vessel | Method | Number of Microtubers (Microtubers/vessel) | | | Weight (g/vessel) | Number of Vessels |
|---|---|---|---|---|---|---|
| | | 0.1 g or more | 0.5 g or more | 1 g or more | | |
| 2L | 8 hr - 1 week | 80.3** | 27.5 | 15.5 | 54.7 | 6 |
| 2L | 8 hr - 2 weeks | 75.9** | 32.4** | 18.6 | 55.1 | 7 |
| 2L | 16 hr - 2 weeks | 65.8** | 40.8** | 26.2** | 65.8 | 6 |
| 2L | First Conventional Method (control) | 45.1 | 23.3 | 16.1 | 51.3 | 7 |
| 4L | 8 hr - 1 week | 121.4** | 46.4 | 31.0 | 94.2 | 5 |
| 4L | First Conventional Method (control) | 91.2 | 42.0 | 29.0 | 94.4 | 6 |

**Those having not less than 1% significance based on the control group.

On the other hand, in the method of the present invention employing 16-hour daylength, the formation of microtubers was observed about one week after the beginning of the culture in the dark as in the first conventional method (control). However, the growth of microtubers thereafter was more rapid than in the first conventional method.

(iii) In the methods employing the 8-hour daylength or 16-hour daylength, the senescence of the stems and leaves in the later stage of the microtuber-formation phase proceeded more quickly than in the first conventional method (control) in spite of the fact that the plants were transferred to the dark at a later time than in the first conventional method, so that mature, high quality microtubers were obtained. This was more prominent in the method employing the 16-hour daylength than that employing the 8-hour daylength.

EXAMPLE 3

Using cultured plantlets of potato (variety: Lemhi Russet, plants maintained in Tissue-Grown Corporation were grown), the effects of the 8-hour daylength after replacement of the medium were examined as in Example 2.

As can be seen from the results shown in Table 4, the number of microtubers produced was larger than in the first conventional method (control).

TABLE 4

Effects of Illumination Before and After Replacement of the Medium

| Volume of Vessel | Method | Number of Microtubers (Microtubers/vessel) | | | Weight (g/vessel) | Number of Vessels |
|---|---|---|---|---|---|---|
| | | 0.1 g or more | 0.5 g or more | 1 g or more | | |
| 2L | 8 hr - 1 week | 32.3 | 24.2* | 16.2* | 56.5 | 6 |
| 2L | First Conventional Method (control) | 24.8 | 16.6 | 12.2 | 53.6 | 5 |

*Those having not less than 5% significance based on the control group.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for producing potato microtubers, said method comprising culturing potato plants in a medium containing low sugar under illumination, followed by culture in a medium containing high sugar in the dark, wherein the improvement comprises:

(a) culturing potato plants in a medium containing 0.5–5% w/v sugar under an illumination regimen of about 12 to about 24 hours per day for about 3 to about 6 weeks; and (b) culturing the resulting potato plants in a medium containing 6–10% w/v sugar for about 1 to about 4 weeks under an illumination regimen of either about 6 to about 12 hours per day or about 12 to about 24 hours per day prior to culturing said plants in the dark to produce said microtubers.

2. The method of claim 1, wherein said sugar of step (a) and step (b) is at least one member selected from the group consisting of sucrose, glucose, fructose, and maltose.

3. The method of claim 2, wherein said sugar of step (a) and step (b) is sucrose.

4. The method of claim 1, wherein said sugar of step (b) is 8% w/v sucrose.

5. The method of claim 1, wherein said medium of step (b) is a member selected from the group consisting of Murashige and Skoog's medium containing 8% w/v sucrose at pH 5.8, White's medium containing 8% w/v sucrose at pH 5.8, and Linsmayer and Skoog's medium containing 8% w/v sucrose at pH 5.8.

6. The method of claim 5, wherein said medium of step (b) is Murashige and Skoog's medium containing 8% w/v sucrose at pH 5.8.

7. The method of claim 1, wherein said potato plants of step (b) are cultured under said illumination regimen of about 6 to about 12 hours per day of step (b) for about one week to produce small microtubers.

8. The method of claim 1, wherein said potato plants of step (b) are cultured under said illumination regimen of about 12 to about 24 hours per day of step (b) for about two weeks to produce large microtubers.

9. The method of claim 1, wherein said culturing under illumination of step (a) comprises liquid aeration culture at 18°–25° C. under illumination at 3,000 to 10,000 lux at an aeration rate of 0.02 to 0.5 liter/liter.minute.

10. The method of claim 9, wherein said culturing under illumination of step (a) comprises liquid aeration culture at 18° to 22° C. under illumination at 4,000 to 6,000 lux at an aeration rate of 0.2 to 0.4 liter/liter.min.

11. The method of claim 1, wherein said culturing said potato plants in the dark of step (b) is carried out for 3 to 10 weeks.

12. The method of claim 11, wherein said culturing said potato plants in the dark of step (b) comprises liquid aeration culture at 18°–25° C. at an aeration rate of 0.02 to 0.5 liter/liter.min.

13. The method of claim 12, wherein said culturing said potato plants in the dark of step (b) comprises liquid aeration culture at 18° to 22° C. at an aeration rate of 0.2 to 0.4 liter/liter.min.

14. A method for producing potato microtubers, comprising, in the order mentioned, the steps of:

culturing potato plants in a medium containing 0.5–5% w/v sugar under an illumination regimen of about 12 to about 24 hours per day for about 3 weeks to about 6 weeks, culturing the resulting potato plants in a medium containing 6–10% w/v sugar for about 1 to about 4 weeks under an illumination regimen of either about 6 to about 12 hours per day or about 12 to about 24 hours per day, and culturing said potato plants in the dark until microtubers are produced.

15. A method for producing potato microtubers, said method comprising culturing potato plants in a medium containing low sugar under illumination, followed by culture in a medium containing high sugar in the dark, wherein the improvement comprises:

culturing Russet potato plants in a medium containing 0.5–5% w/v sugar under an illumination regimen of about 12 to about 24 hours per day for about 3 to about 6 weeks;

culturing the resulting potato plants in a vessel having a volume of 2–4 liters containing 0.6 to 1 liter of medium at pH 5.8, containing 6–10% w/v sugar, at an aeration rate of 0.35–0.80 liters/minute at a temperature of 20° C. for about 1 to about 4 weeks under a dark/light cycle of 8 or 16 hours light at 5,000 lux; and then culturing said potato plants in the dark until microtubers are produced.

16. The method of claim 15, wherein said plants are cultured in said medium containing 6–10% w/v sugar for about two weeks under a dark/light cycle of 16 hours light.

17. The method of claims 15, wherein said sugar is sucrose.

18. A method for producing potato microtubers comprising, in the order mentioned, the steps of:

1) culturing nodal cuttings of Russet potato plants in a medium having a pH in the range from 4 to 8, containing 0.5 to 5% w/v sugar, in a vessel having a volume of 2 to 4 liters containing 0.6 to 1 liter of said medium, under an illumination regimen of about 12 to about 24 hours per day at 3,000 to 10,000 lux, at a temperature of 18°–25° C., at an aeration rate of 0.35 to 0.8 liters/minute, for about 3 weeks to about 6 weeks;

2) culturing potato plants produced in step 1) in a medium having a pH in the range from 4 to 8, containing 6 to 10% w/v sugar, in a vessel having a volume of 2 to 4 liters containing 0.6 to 1 liter of said medium, under an illumination regimen of about 6 to about 12 hours per day or about 12 to about 24 hours per day at 3,000 to 10,000 lux, at a temperature of 18° to 25° C., at an aeration rate of 0.35 to 0.8 liters/minute, for about 1 week to about 4 weeks; and 3) culturing potato plants produced in step 2) under the same conditions as in step 2), except that said potato plants are cultured in the dark, until microtubers are produced.

19. The method of claims 18, wherein said culturing of step 2) is carried out under an illumination regimen of about 12 to about 24 hours per day for about 2 weeks.

20. The method of claim 18, wherein said sugar is sucrose.

* * * * *